(12) United States Patent
Sakamoto et al.

(10) Patent No.: US 11,756,676 B2
(45) Date of Patent: Sep. 12, 2023

(54) MEDICAL IMAGE PROCESSING APPARATUS, CONTROL METHOD FOR THE SAME, AND PROGRAM

(71) Applicant: CANON KABUSHIKI KAISHA, Tokyo (JP)

(72) Inventors: Tsuyoshi Sakamoto, Tokyo (JP); Yusuke Imasugi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/523,399

(22) Filed: Nov. 10, 2021

(65) Prior Publication Data

US 2022/0068470 A1    Mar. 3, 2022

Related U.S. Application Data

(63) Continuation of application No. 16/711,158, filed on Dec. 11, 2019, now Pat. No. 11,200,977, which is a (Continued)

(30) Foreign Application Priority Data

Oct. 30, 2015  (JP) ................................ 2015-215286
Oct. 7, 2016   (JP) ................................ 2016-199458

(51) Int. Cl.
*G16H 30/20*    (2018.01)
*G16H 30/40*    (2018.01)
(Continued)

(52) U.S. Cl.
CPC .............. *G16H 30/40* (2018.01); *G06T 5/30* (2013.01); *G06T 7/0012* (2013.01); *G16H 30/20* (2018.01);
(Continued)

(58) Field of Classification Search
CPC ....... G16H 30/40; G16H 30/20; G06T 7/0012
See application file for complete search history.

(56) References Cited

U.S. PATENT DOCUMENTS

2012/0275682 A1\* 11/2012 Ihara ..................... G06T 7/0012
                                                         382/128

OTHER PUBLICATIONS

Cassot et al, "A Novel Three-Dimensional Computer-Assisted Method fora Quantitative Study of Microvascular Networks of the Human Cerebral Cortex", 2006, Microcirculation 13.1, 18 pages (Year: 2006).\*

(Continued)

*Primary Examiner* — David F Dunphy
(74) *Attorney, Agent, or Firm* — Canon U.S.A., Inc. IP Division

(57) ABSTRACT

A plurality of analysis functions each corresponding to an organ are managed, and organ information is stored in such a manner as to correlate with a corresponding type of analysis function. The organ information indicates which of a plurality of regions included in the organ is to be subjected to thinning. Specification of one of the analysis functions is received from a user, and medical image data is acquired. A plurality of regions of an organ included in the acquired medical image data are identified. The identified plurality of regions of the organ, a region to be subjected to thinning is determined on the basis of the stored organ information and the received type of the analysis function. Thinning is performed on the determined region of the organ. An image of the thinned region is displayed together with an image of a region not subjected to thinning.

9 Claims, 14 Drawing Sheets

Related U.S. Application Data continuation of application No. 15/962,991, filed on Apr. 25, 2018, now Pat. No. 10,535,428, which is a continuation of application No. PCT/JP2016/081981, filed on Oct. 28, 2016.

(51) Int. Cl.
*G06T 5/30* (2006.01)
*G06T 7/00* (2017.01)

(52) U.S. Cl.
CPC ............... *G06T 2207/20036* (2013.01); *G06T 2207/30016* (2013.01); *G06T 2207/30048* (2013.01); *G06T 2207/30056* (2013.01); *G06T 2207/30061* (2013.01); *G06T 2207/30101* (2013.01)

(56) References Cited

OTHER PUBLICATIONS

Xiaojun Jing, Image Processing Technology and its Application, Dec. 2, 2021.

* cited by examiner

500

| ANALYSIS FUNCTION | PARTS | THINNING FLAG |
|---|---|---|
| LIVER ANALYSIS | LIVER PARENCHYMA | 0 |
| | INFERIOR VENA CAVA | 0 |
| | ARTERIES | 0 |
| | PORTAL VEIN | 1 |
| | VEINS | 1 |
| HEART ANALYSIS | HEART PARENCHYMA | 0 |
| | AORTA | 0 |
| | RIGHT CORONARY ARTERY | 1 |
| | LEFT CORONARY ARTERY | 1 |
| ⋮ | ⋮ | ⋮ |

MEDICAL IMAGE PROCESSING APPARATUS, CONTROL METHOD FOR THE SAME, AND PROGRAM

CROSS-REFERENCE TO RELATED APPLICATIONS

This application is a continuation of U.S. patent application Ser. No. 16/711,158, filed on Dec. 11, 2019, which is a continuation of U.S. patent application Ser. No. 15/962,991, filed on Apr. 25, 2018 and now issued as U.S. Pat. No. 10,535,428 on Jan. 14, 2020, which is a Continuation of International Patent Application No. PCT/JP2016/081981, filed Oct. 28, 2016, which claims the benefit of Japanese Patent Application No. 2015-215286, filed Oct. 30, 2015 and No. 2016-199458, filed Oct. 7, 2016, both of which are hereby incorporated by reference herein in their entirety.

TECHNICAL FIELD

The present invention relates to a medical image processing apparatus, a control method for the same, and a program.

BACKGROUND ART

When cancer is found in an organ, various treatment plans are developed in accordance with the stage of the cancer.

Examples of typical surgical approaches to liver cancer include partial liver resection. The examples also include living liver transplantation which transfers a healthy liver to a patient who would become dysfunctional as a result of liver cancer. These procedures both involve controlling the liver volume. If the liver rapidly loses equal to or more than 40% of its volume, the risk of liver failure increases significantly. Therefore, it is essential to plan in advance the extent of surgery and predict the post-treatment conditions of the patient. A technique that uses 3D computed tomography (3D-CT) to estimate the liver volume from the number of pixels in segments of the liver has emerged and become widely used, and currently its effectiveness is known.

PTL 1 (described below) discloses a mechanism that provides an image suitable for observation of the course of blood vessels in the vicinity of a cut surface.

CITATION LIST

Patent Literature

PTL 1 Japanese Patent Laid-Open No. 2014-18619

For partial liver resection and living liver transplantation, segments of the liver are estimated before surgery on the basis of the course of blood vessels. For surgery of an organ (e.g., liver) having an intricate structure of blood vessels, it is essential to know the course of blood vessels in advance. For the liver, this is done by observing, from every angle, the course of the portal and hepatic veins reproduced on the computer.

The central structure of each blood vessel is of most importance in liver surgical procedures. However, blood vessel structures reproduced on the computer naturally appear without change in the size of central blood vessels. As a result, the blood vessel structures overlap one another and this makes it difficult to understand the course of blood vessels in detail. Therefore, it is preferable that blood vessels be displayed in a manner which allows observation of their central structures.

An object of the present invention is to provide a mechanism that can facilitate thinning and display of a region the user wants to display in thinned mode.

SUMMARY OF INVENTION

To achieve the object described above, a medical image processing apparatus according to the present invention includes managing means for managing a plurality of analysis functions each corresponding to an organ; storage means for storing organ information in such a manner as to correlate the organ information with a corresponding type of analysis function managed by the managing means, the organ information indicating which of a plurality of regions included in the organ is to be subjected to thinning; receiving means for receiving specification of one of the analysis functions managed by the managing means; acquiring means for acquiring medical image data; identifying means for identifying a plurality of regions of an organ included in the medical image data; instruction receiving means for receiving an instruction to perform thinning on the organ; determining means for determining, in accordance with the instruction received by the instruction receiving means, which of the plurality of regions of the organ identified by the identifying means is to be subjected to thinning, on the basis of the organ information stored by the storage means and the type of the analysis function received by the receiving means; generating means for generating thinned surface shape data by performing thinning on medical image data of the region of the organ determined by the determining means; and display control means for performing control in such a manner that an image representing the thinned surface shape data is displayed together with an image of a region not subjected to thinning by the generating means.

Further features of the present invention will become apparent from the following description of exemplary embodiments with reference to the attached drawings.

DESCRIPTION OF EMBODIMENTS

Hereinafter, embodiments of the present invention will be described with reference to the drawings.

Figure 1:
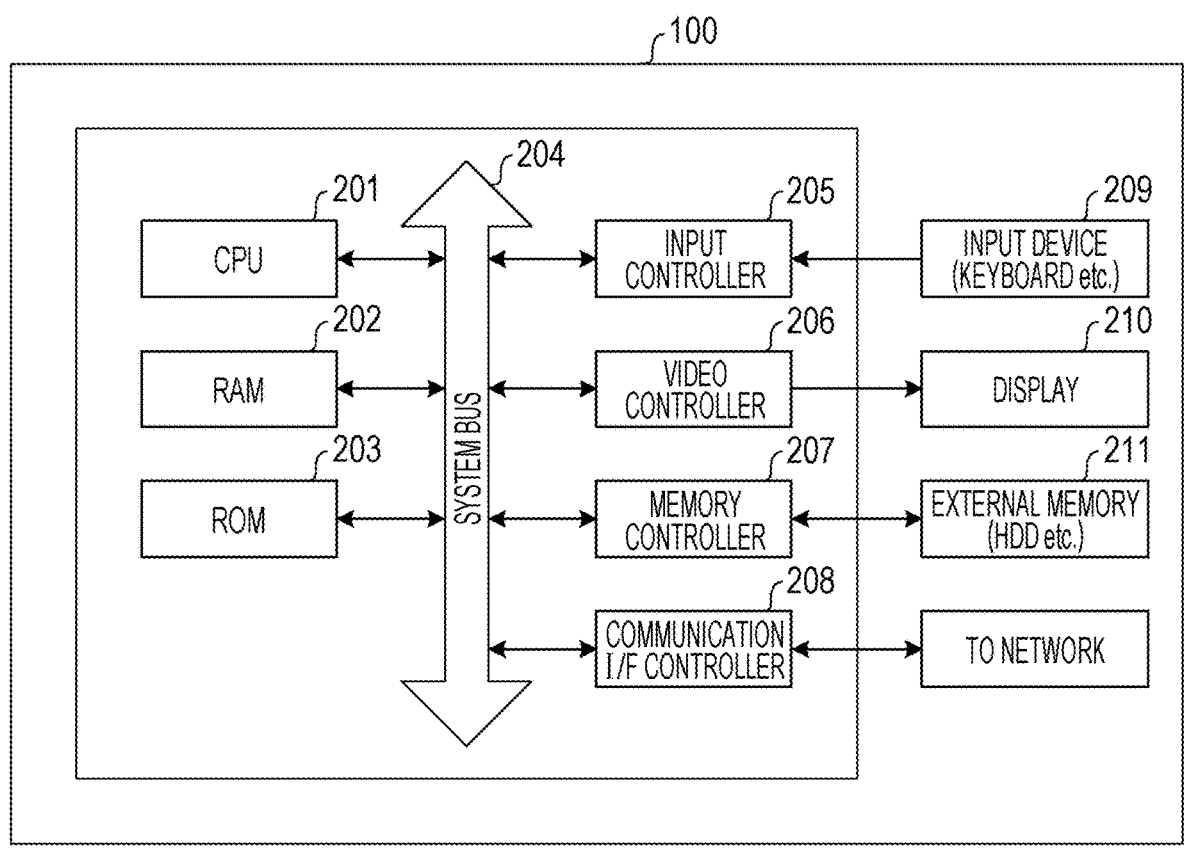
FIG. 1 is a diagram illustrating a hardware configuration of a medical image processing apparatus 100 according to an embodiment of the present invention.

First, a hardware configuration of a medical image processing apparatus 100 according to an embodiment of the present invention will be described using FIG. 1. Note that the hardware configuration of the medical image processing apparatus 100 illustrated in FIG. 1 is merely an example and various other configurations are possible depending on the intended use or purpose.

The medical image processing apparatus 100 includes a CPU 201, a RAM 202, a ROM 203, a system bus 204, an input controller 205, a video controller 206, a memory controller 207, a communication I/F controller 208, an input device 209, a display 210, and an external memory 211.

The CPU 201 performs overall control of devices and controllers connected to the system bus 204.

The RAM 202 serves, for example, as a main memory or work area for the CPU 201. For execution of processing, the CPU 201 loads, for example, an appropriate program into the RAM 202 and implements various operations by executing the program.

The ROM 203 or the external memory 211 stores a basic input/output system (BIOS) and an operating system, which are control programs of the CPU 201, and various other programs (described below) required for implementing functions executed by various devices.

The input controller 205 controls inputs from a pointing device (input device 209), such as a keyboard or mouse.

The video controller 206 controls display of a display device, such as the display 210. The display 210 (display unit) is, for example, a CRT or liquid crystal display.

The memory controller 207 controls access to the external memory 211 (such as a hard disk, a flexible disk, or a card type memory connected to a PCMCIA card slot via an adapter) that stores, for example, a boot program, a browser software program, various applications, font data, user files, and various types of data.

Note that the CPU 201 enables display on the display 210, for example, by expanding (rasterizing) an outline font in a display information area in the RAM 202. Also, the CPU 201 allows the user to point with a mouse cursor (not shown) or the like on the display 210.

Various programs the medical image processing apparatus 100 of the present invention uses to perform various types of processing (described below) are stored in the external memory 211. These programs are loaded into the RAM 202 as necessary, and thus executed by the CPU 201. Definition files, various information tables, and medical images used by a program according to the present invention are stored in the external memory 211. The medical images may be stored in an external server and acquired therefrom by the medical image processing apparatus 100.

The description of the hardware configuration of the medical image processing apparatus 100 illustrated in FIG. 1 ends here.

A functional configuration diagram of the medical image processing apparatus 100 will now be described using FIG. 2.

The medical image processing apparatus 100 includes such functional units as a managing unit 2001, a storage unit 2002, an acquiring unit 2003, an identifying unit 2004, an instruction receiving unit 2005, a determining unit 2006, a generating unit 2007, and a display control unit 2008.

The managing unit 2001 manages a plurality of analysis functions each corresponding to an organ. The storage unit 2002 stores organ information in such a manner as to correlate it with the type of analysis function managed. The organ information is information indicating which of a plurality of regions included in the organ is to be thinned (i.e., subjected to thinning). The acquiring unit 2003 acquires medical image data. The identifying unit 2004 identifies a plurality of regions of an organ included in the medical image data. The instruction receiving unit 2005 receives an instruction to perform thinning on the organ. The determining unit 2006 determines which of the plurality of regions of the organ identified in the medical image data is to be thinned, on the basis of the organ information stored in the storage unit and the type of analysis function specified by the user. The generating unit 2007 is a functional unit that performs thinning on the region of the organ determined by the determining unit and generates thinned shape data. The display control unit 2008 performs control in such a manner that an image representing the thinned shape data generated, by the generating unit, from one of the plurality of regions of the organ is displayed together with an image of a region not subjected to thinning.

Figure 2:
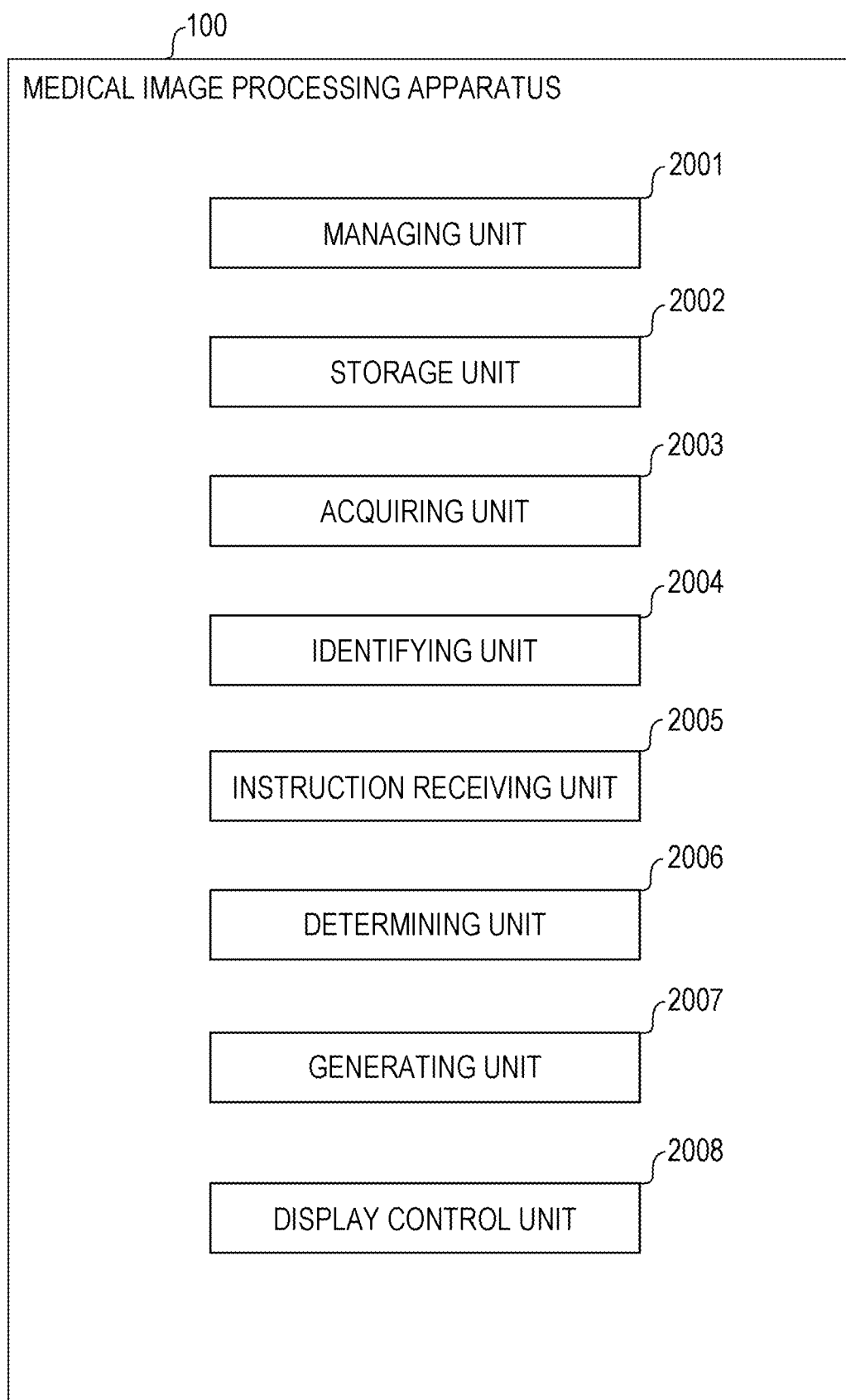
FIG. 2 is a diagram illustrating a functional configuration of the medical image processing apparatus 100 according to the embodiment of the present invention.

The description of the functional configuration of the medical image processing apparatus 100 illustrated in FIG. 2 ends here.

First Embodiment

A first embodiment of the present invention will now be described in detail using the flowchart of FIG. 3.

In step S301, the CPU 201 of the medical image processing apparatus 100 receives specification of medical image data in accordance with an instruction from the user. In the present embodiment, the medical image data is volume data of a subject acquired by being captured by a modality, such as a computed tomography (CT) machine or magnetic resonance imaging (MRI) machine.

Figures 4, 5:
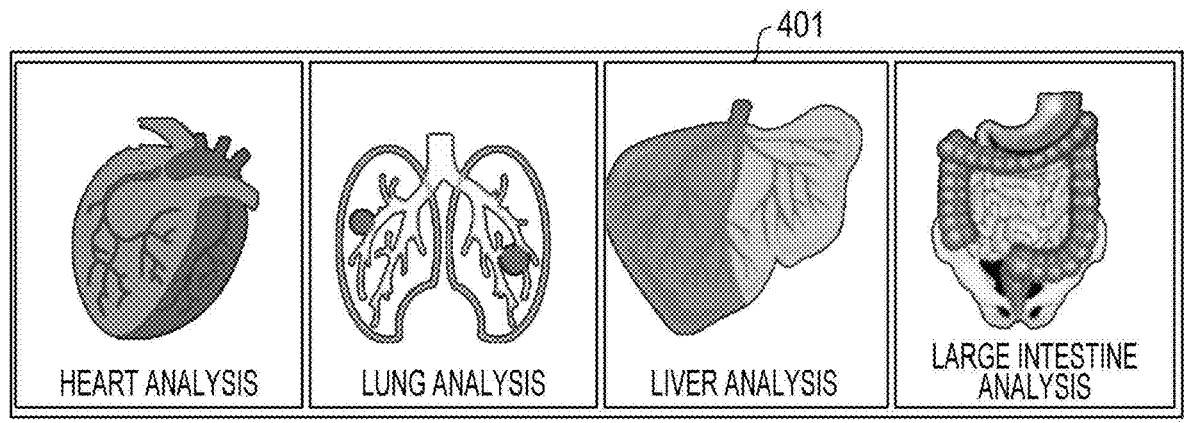
FIG. 4 shows an exemplary screen capable of receiving selection of an analysis function according to the embodiment of the present invention.
FIG. 5 is a data table representing an example of an analysis function table 500 according to the embodiment of the present invention.

In step S302, the CPU 201 of the medical image processing apparatus 100 receives selection of an analysis function from the user. For example, by receiving selection of an icon on the selection screen shown in FIG. 4, the CPU 201 receives selection of an analysis function corresponding to the icon. Although the present embodiment describes processing performed in response to a press of a liver analysis icon 401, the CPU 201 may receive selection of an analysis function for analyzing a different site, such as a heart.

In step S303, the CPU 201 of the medical image processing apparatus 100 acquires, from the external memory 211, settings corresponding to the analysis function for which the selection has been received in step S302. Specifically, the settings corresponding to the analysis function include information for configuring the screen shown in FIG. 7 and information for analyzing the organ (i.e., analysis object). Each of the analysis functions is assigned a different button on the screen. When the user presses a button, settings using the medical image data selected in step S301 are acquired on the basis of the settings corresponding to the analysis function. In the present embodiment, settings corresponding to the liver analysis selected in step S302 are acquired. The settings corresponding to the liver analysis include parts information which is information on parts (regions) included in the liver, such as liver parenchyma, inferior vena cava, arteries, portal vein, and veins.

In step S304, the CPU 201 of the medical image processing apparatus 100 receives specification of segments that are extracted from the medical image data in such a manner as to correlate with the parts information on each of the liver parenchyma, inferior vena cava, arteries, portal vein, and veins.

In step S305, the CPU 201 of the medical image processing apparatus 100 stores the medical image data segments for which the specification has been received in step S304, in such a manner that they correlate with the corresponding parts information.

The segments described above may be extracted from the medical image data and correlated with the parts information by manually extracting the segments while the parts information is identified by the user. Alternatively, the segments may be automatically extracted on the basis of extraction conditions stored in advance in such a manner as to correlate with the analysis function, and then stored in such a manner as to correlate with the parts information.

In step S306, the CPU 201 of the medical image processing apparatus 100 receives selection of one of parts buttons, each corresponding to one piece of organ parts information. That is, a parts button is a button provided for each piece of parts information, such as a veins button 701 shown in FIG. 7.

Figure 7:
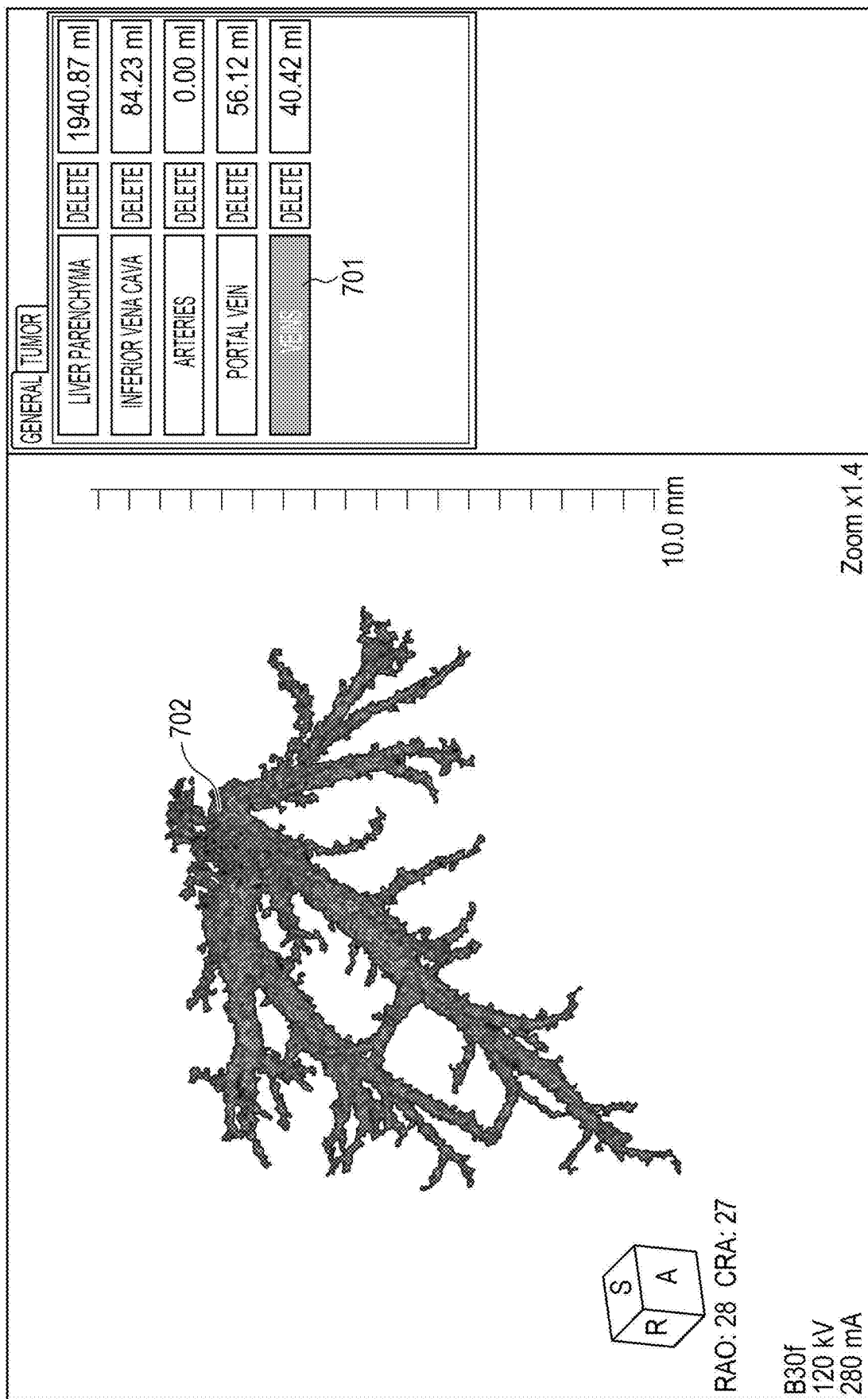
FIG. 7 shows an exemplary screen on which "veins" is selected and veins are displayed according to the embodiment of the present invention.

In step S307, the CPU 201 of the medical image processing apparatus 100 displays, on a display screen, a part corresponding to the parts button selected in step S306. For example, if the selection of the veins button 701 has been received, veins 702 are displayed as shown in FIG. 7.

Figure 3:
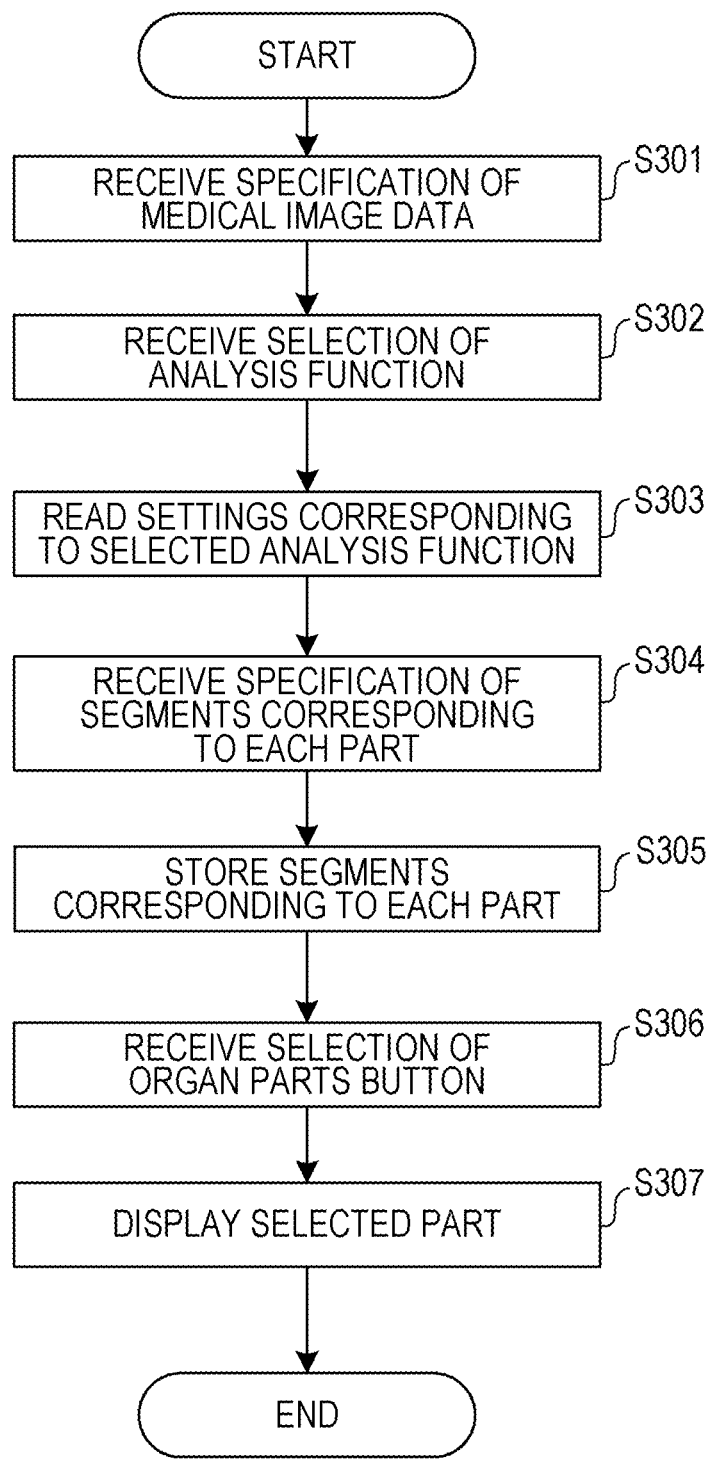
FIG. 3 is a flowchart illustrating a detailed flow of processing according to the embodiment of the present invention.

The description of the flowchart of FIG. 3 ends here. Performing the process illustrated in FIG. 3 makes it possible to store segments corresponding to each organ part included in the medical image data for which the specification has been received in step S301, and also to display the part corresponding to the selected parts information on the display unit.

Figure 8:
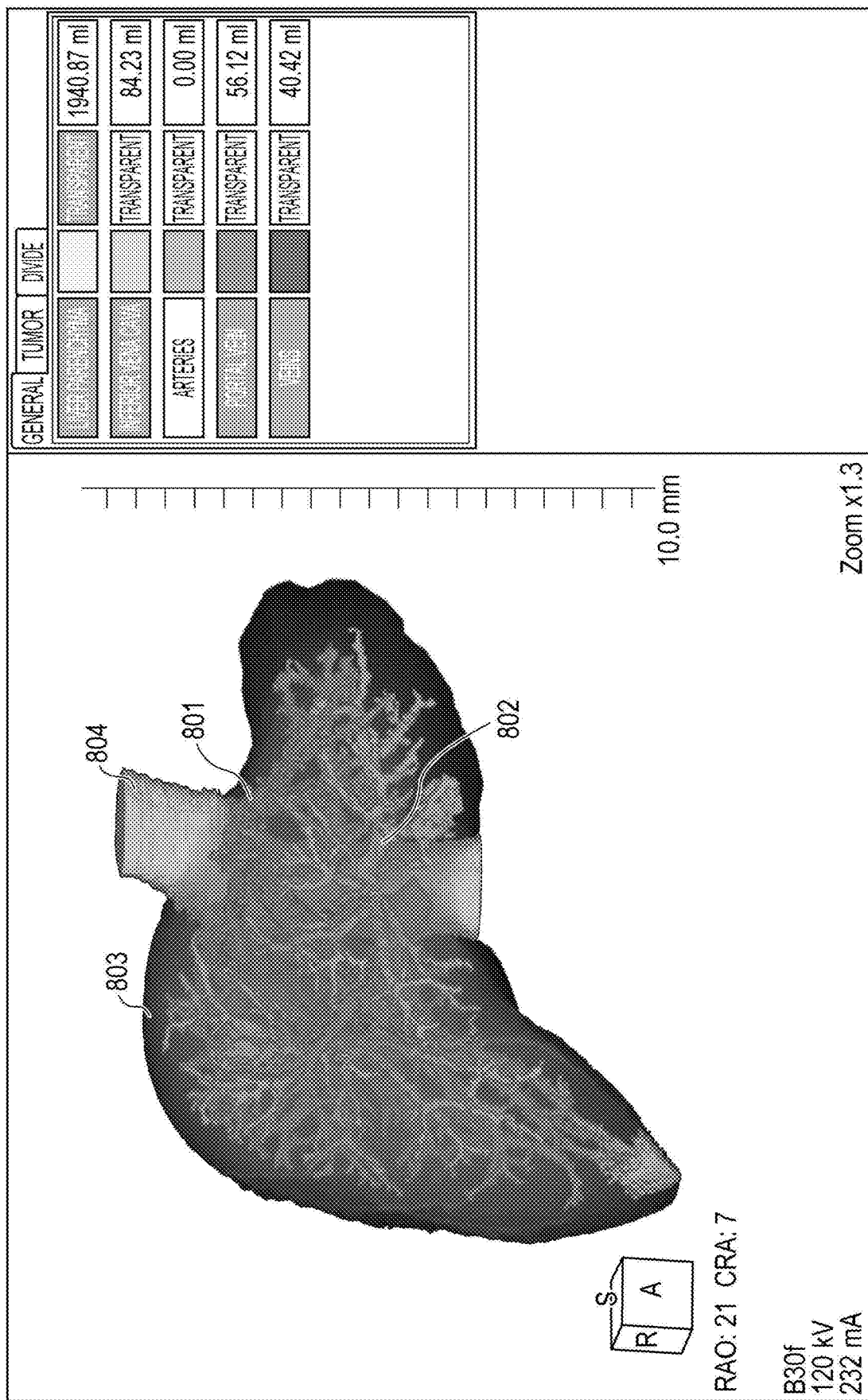
FIG. 8 shows an exemplary screen on which a plurality of "parts" are selected and a plurality of parts are displayed according to the embodiment of the present invention.

If a parts button is turned on or off while a part is being displayed in this manner, a part corresponding to the parts button which has been turned on is displayed and a part corresponding to the parts button which has been turned off is hidden. That is, for example, when parts buttons for the liver parenchyma, inferior vena cava, portal vein, and veins are pressed as shown in FIG. 8, images of a liver parenchyma 803, an inferior vena cava 804, a portal vein 802, and veins 801 are displayed on the display unit.

Figure 6:
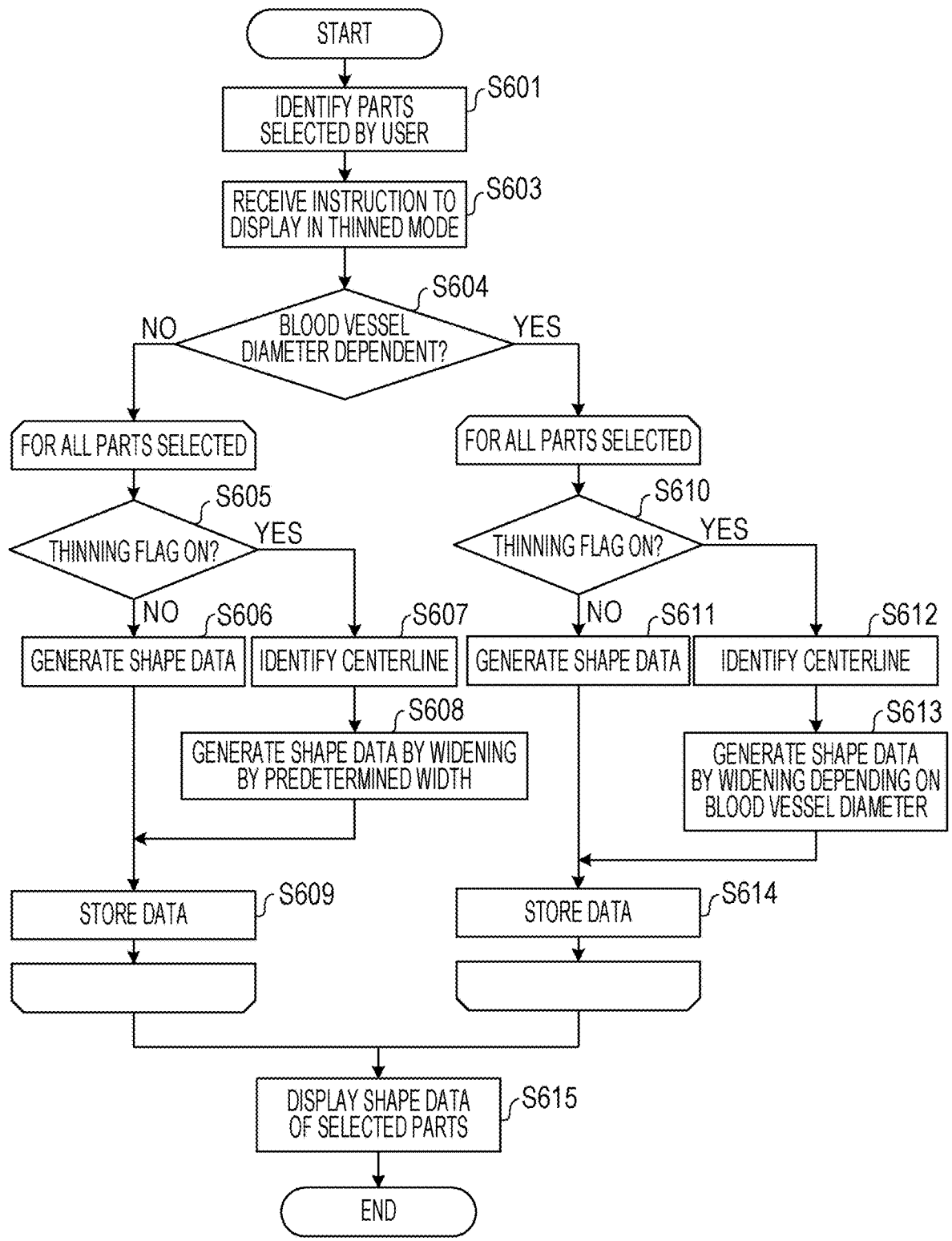
FIG. 6 is a flowchart illustrating a detailed flow of processing according to the embodiment of the present invention.

After the segments corresponding to each of the organ parts are stored as described above, a parts thinning process illustrated in the flowchart of FIG. 6 is enabled.

The flowchart of FIG. 6 will now be described.

In step S601, the CPU 201 of the medical image processing apparatus 100 identifies parts selected by the user. Specifically, by determining which parts buttons are pressed, the CPU 201 identifies the parts selected by the user.

In step S603, the CPU 201 of the medical image processing apparatus 100 determines whether an instruction to display an organ in thinned mode has been received. Specifically, if a press of a surface creation button 912 (see FIG. 9) is received while a checkbox 910 for indicating whether to perform thinning is checked by the user, the CPU 201 determines that an instruction to display in thinned mode has been received.

Upon receiving the press of the surface creation button 912, the CPU 201 of the medical image processing apparatus 100 determines, in step S604, whether a "blood vessel diameter dependent" checkbox 911 is checked (i.e., whether the checkbox has been selected by the user). If the CPU 201 determines that the "blood vessel diameter dependent" checkbox 911 is checked, the process proceeds to step S610, and otherwise proceeds to step S605.

The flow from step S605 to step S609 is a routine flow performed for all the parts identified in step S601.

In step S605, the CPU 201 of the medical image processing apparatus 100 determines, for one of the parts selected in step S601, whether the corresponding flag in thinning flag 503 is on.

Specifically, first, the CPU 201 acquires an analysis function table 500 (such as that of FIG. 5) stored in the external memory 211. The analysis function table 500 has such fields as analysis function 501 showing the types of analysis functions, parts 502 showing organ parts corresponding to each of the analysis functions, and the thinning flag 503 containing flags each indicating whether to perform thinning on a corresponding part in the parts 502. These elements in the analysis function 501, parts 502 and thinning flag 503 are stored in such a manner as to correlate with each other. On the basis of a flag in the thinning flag 503 for the part corresponding to the analysis function selected by the user in step S302, the CPU 201 acquires flag information for the selected part from the analysis function table 500. The CPU 201 then makes a determination in such a manner that if the acquired flag information is on (set to 1), the process proceeds to step S607, and otherwise proceeds to step S606.

In the present embodiment, where the selected analysis function is liver analysis, only the parts "portal vein" and "veins" are selected to be subjected to thinning in the analysis function table 500. Therefore, if the selected part is "portal vein" or "veins", the process proceeds to step S607, whereas if the selected part is "liver parenchyma", "inferior vena cava", or "arteries", then the process proceeds to step S606. If the selected analysis function is heart analysis, then only when the selected part is "right coronary artery" or "left coronary artery", the process proceeds to step S607 for thinning.

In step S606, the CPU 201 of the medical image processing apparatus 100 generates surface shape data of a part for which the CPU 201 has determined in step S605 that the corresponding flag in the thinning flag 503 is off (or set to 0). The surface shape data is, for example, polygon data generated by marching cubes (which is a known technique) on the basis of medical image data corresponding to the part.

In step S607, the CPU 201 of the medical image processing apparatus 100 identifies the centerline of the part on which determination has been made in step S605. The centerline may be identified, for example, by a technique obtained by extending a two-dimensional thinning technique, such as the Hilditch's algorithm, to three dimensions or a thinning technique obtained by extending a three-dimensional surface thinning technique.

In step S608, the CPU 201 of the medical image processing apparatus 100 generates surface shape data (thinned surface shape data) by widening the centerline identified in step S607 by a predetermined width in a direction orthogonal to the centerline.

In step S609, the CPU 201 of the medical image processing apparatus 100 stores in the external memory 211 the surface shape data generated in step S606 or step S608.

When steps S605 to S609 are completed for all the parts selected in step S601, the process proceeds to step S615.

In step S610, on the basis of the analysis function table 500, the CPU 201 of the medical image processing apparatus 100 determines, for one of the selected parts, whether the corresponding flag in the thinning flag 503 is on, in the same manner as in step S605. If the CPU 201 determines that the corresponding flag in the thinning flag 503 is on, the process proceeds to step S612, and otherwise proceeds to step S611.

In step S611, the CPU 201 of the medical image processing apparatus 100 generates surface shape data of a part for which the CPU 201 has determined in step S610 that the corresponding flag in the thinning flag 503 is off. The surface shape data is, for example, polygon data generated by marching cubes (which is a known technique) on the basis of medical image data corresponding to the part.

In step S612, the CPU 201 of the medical image processing apparatus 100 identifies the centerline of the part for which the CPU 201 has determined in step S610 that the corresponding flag in the thinning flag 503 is on. The technique used here to identify the centerline is the same as that described above.

In step S613, the CPU 201 of the medical image processing apparatus 100 generates surface shape data by widening the centerline identified in step S612 in a direction orthogonal to the centerline in such a manner that the width of the centerline is proportional to the diameter of the blood vessel (tubular structure). A known technique is used to calculate the blood vessel diameter, and the width of the centerline is widened in accordance with the blood vessel diameter determined. That is, surface shape data is generated which represents the blood vessel diameter slightly smaller than the actual blood vessel diameter.

In step S614, the CPU 201 of the medical image processing apparatus 100 stores in the external memory 211 the surface shape data generated in step S611 or step S613.

When steps 5610 to 5614 are completed for all the parts selected in step S601, the process proceeds to step S615.

In step S615, the CPU 201 of the medical image processing apparatus 100 displays the surface shape data of the parts selected in step S601. That is, an image of thinned surface shape data is displayed together with an image of surface shape data of regions not subjected to thinning.

Figure 9:
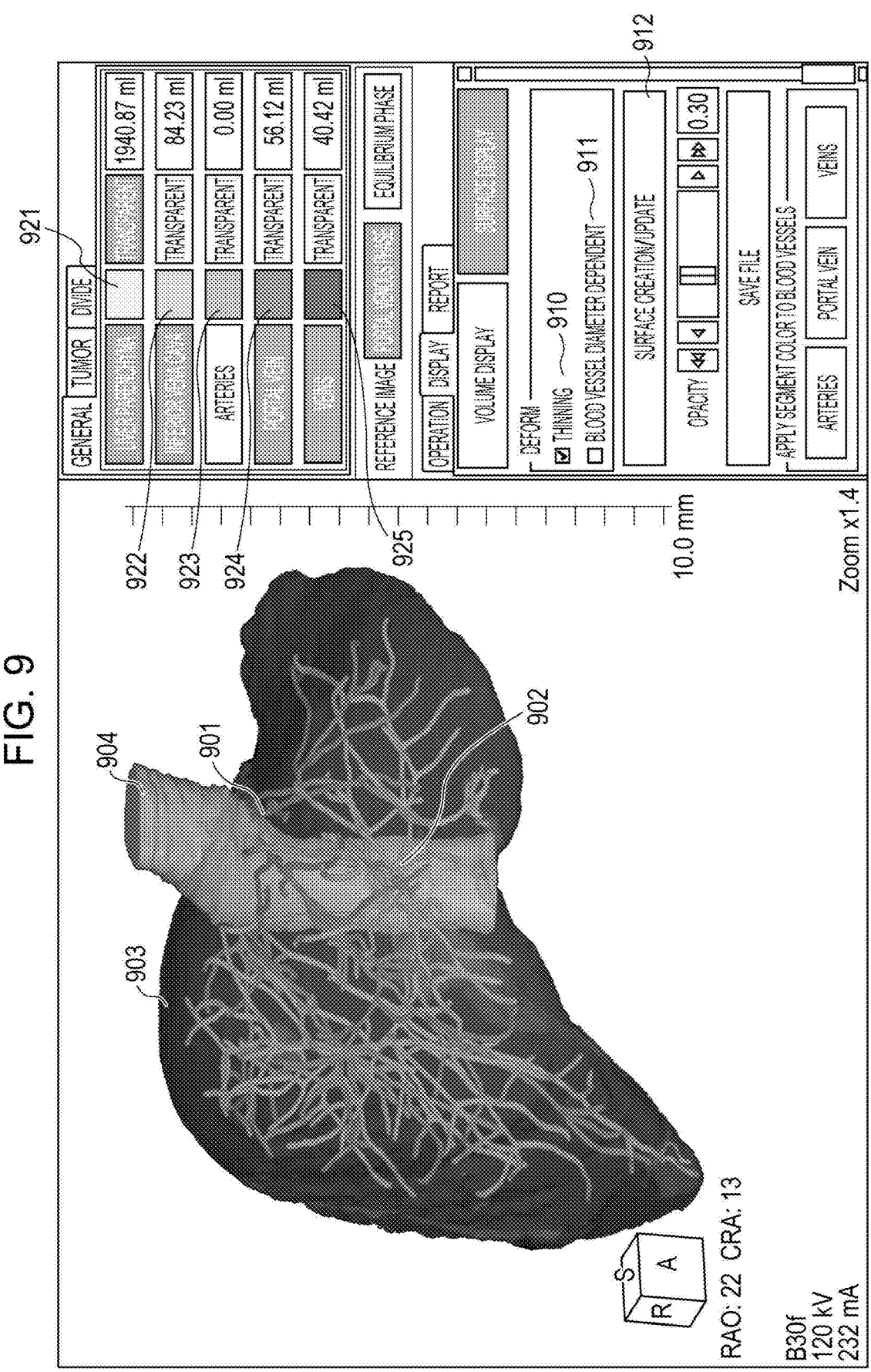
FIG. 9 shows an exemplary screen on which a plurality of "parts" are selected and shape data (surface shape data) obtained by widening the centerline of each of predetermined parts by a predetermined width is displayed, according to the embodiment of the present invention.

The screen shown in FIG. 9 is an exemplary screen that presents an image generated from the surface shape data displayed in step S615 after completion of step S605 to step S609 for all the parts selected in step S601.

In the exemplary screen shown in FIG. 9, only a portal vein 902 and veins 901 for which the corresponding flags in the thinning flag 503 are on in the analysis function table 500 are subjected to thinning, by which they are widened with respect to their centerlines by a predetermined width, and the resulting shapes are displayed. On the other hand, a liver parenchyma 903 (organ parenchyma) and an inferior vena cava 904 are not subjected to thinning and are displayed with their original shapes. As described above, by simply giving an instruction to perform thinning, only parts that are to be thinned can be thinned and displayed by the user. The user can thus be saved the trouble of selecting a part to be thinned each time.

The exemplary screen shown in FIG. 9 allows setting of color information for each part, and provides color information setting buttons (921 to 925) for respective parts. Upon receiving selection of a color information setting button, a color setting screen, which allows setting of colors using RGB values, appears and receives user's specification of colors. The colors specified here are displayed as the colors of the parts corresponding to the color information setting buttons. For example, if the color specified with the color information setting button 921 is pink, the liver parenchyma 903 is displayed in pink. Thus, by setting different colors for the portal vein 902 and the veins 901 that run intricately in the liver parenchyma 903, the course of blood vessels in the liver parenchyma 903 can be displayed in an easily understandable manner. The color information can be preset in such a manner as to correspond to a part extracted from volume data. In this case, the color information is inherited as color information corresponding to a thinned part, so that an image corresponding to the thinned surface shape data is displayed in the corresponding color.

Figure 10:
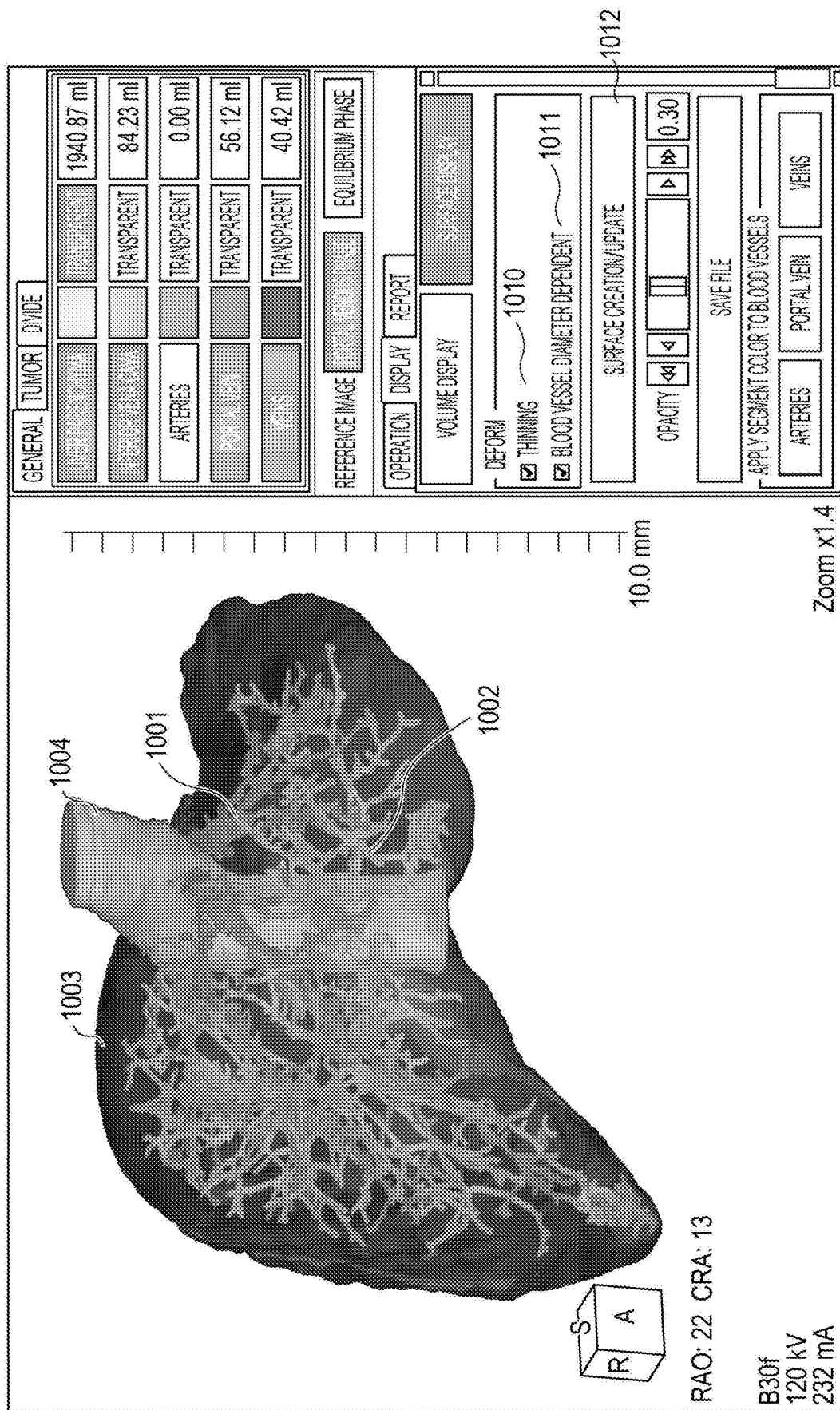
FIG. 10 shows an exemplary screen on which a plurality of "parts" are selected and shape data obtained by widening the centerline of each of predetermined parts in accordance with the blood vessel diameter is displayed, according to the embodiment of the present invention.

The screen shown in FIG. 10 is an exemplary screen that presents the surface shape data displayed in step S615 after completion of step S610 to step S613 for all the parts selected in step S601.

In the exemplary screen shown in FIG. 10, only a portal vein 1002 and veins 1001 for which the corresponding flags in the thinning flag 503 are on in the analysis function table 500 are subjected to thinning, by which they are widened in accordance with their blood vessel diameters. On the other hand, a liver parenchyma 1003 and an inferior vena cava 1004 are not subjected to thinning and are displayed with their original shapes. In FIG. 10, again, by simply giving an instruction to perform thinning, only parts that are to be thinned can be thinned and displayed by the user. The user can thus be saved the trouble of selecting a part to be thinned each time. Additionally, since the centerlines are widened in accordance with the blood vessel diameters, the parts can be displayed in such a manner that the courses of blood vessels are easily identifiable even though the displayed blood vessels are closer to actual ones than in the case of FIG. 9.

In FIG. 10, as in FIG. 9, color information can be set for each part. Upon receiving selection of a color information setting button, a color setting screen, which allows setting of colors using RGB values, appears and receives user's specification of colors. The colors specified here are displayed as the colors of the parts corresponding to the color information setting buttons. Thus, for example, by setting different colors for the portal vein 902 and the veins 901 that run intricately in the liver parenchyma 903, the course of blood vessels in the liver parenchyma 903 can be displayed in an easily understandable manner.

Figure 11:
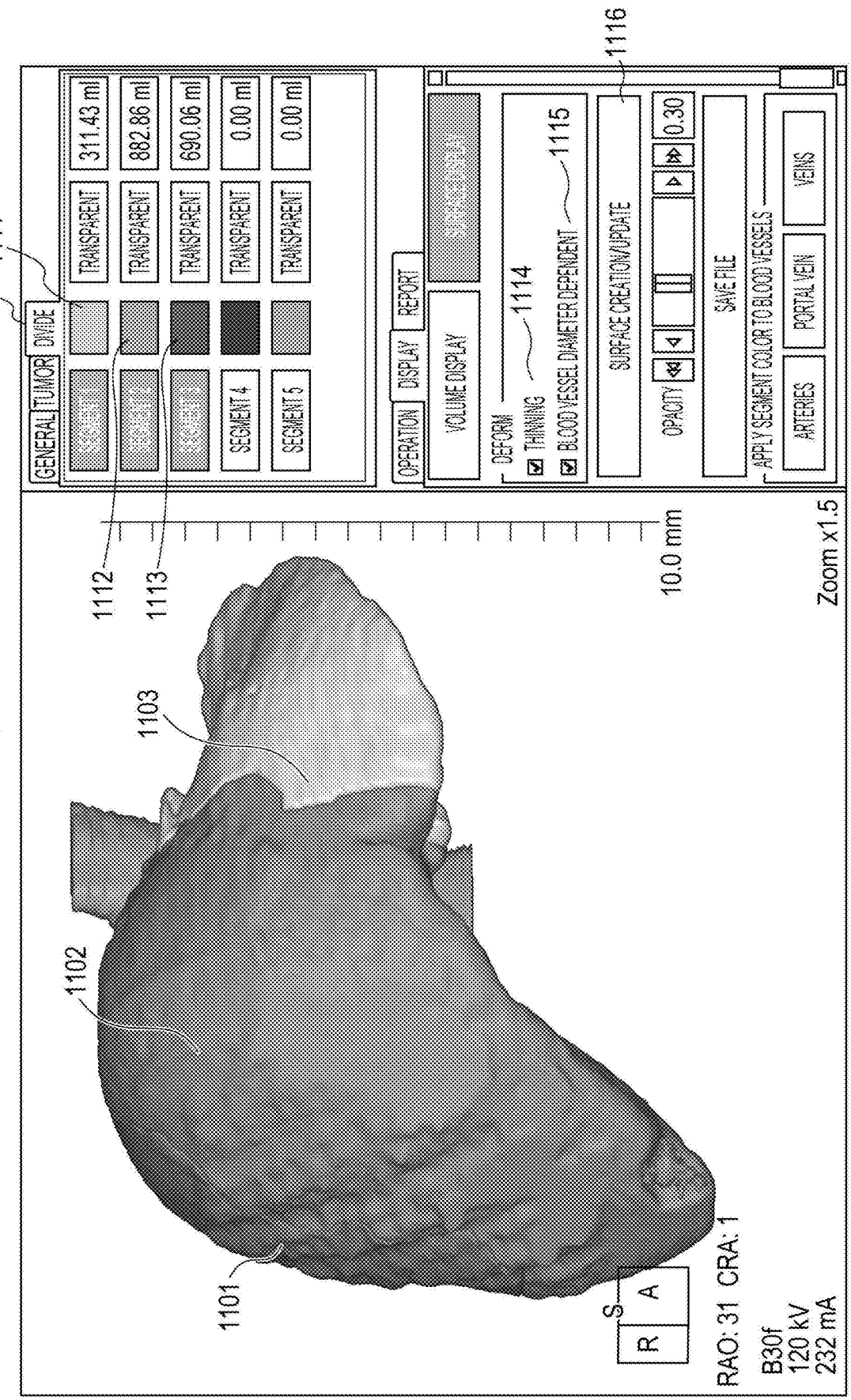
FIG. 11 shows an exemplary screen on which an organ is divided into predetermined segments and the segments are identifiably displayed.

Additionally, when, as illustrated in FIG. 11, selection of a divide button 1110 (division instruction) is received, for example, specification for dividing the liver parenchyma 903 into a plurality of segments, such as a "left hepatic vein perfusion segment 1103", a "middle hepatic vein perfusion segment 1102", and a "right hepatic vein perfusion segment 1101", in accordance with the course of veins can be received. The segments may be specified manually by the user or may be specified using a known technique. When the user receives selection of color information setting buttons 1111 to 1113 for the segments, a color setting screen which enables setting of colors using RGB values is displayed, and this allows setting of colors. Colors specified using the color information setting buttons are applied to the three segments and displayed. Specifically, a color specified using the color information setting button 1111 is applied to the "left hepatic vein perfusion segment 1103", a color specified using the color information setting button 1112 is applied to the "middle hepatic vein perfusion segment 1102", and a color specified using the color information setting button 1113 is applied to the "right hepatic vein perfusion segment 1101".

Figure 12:
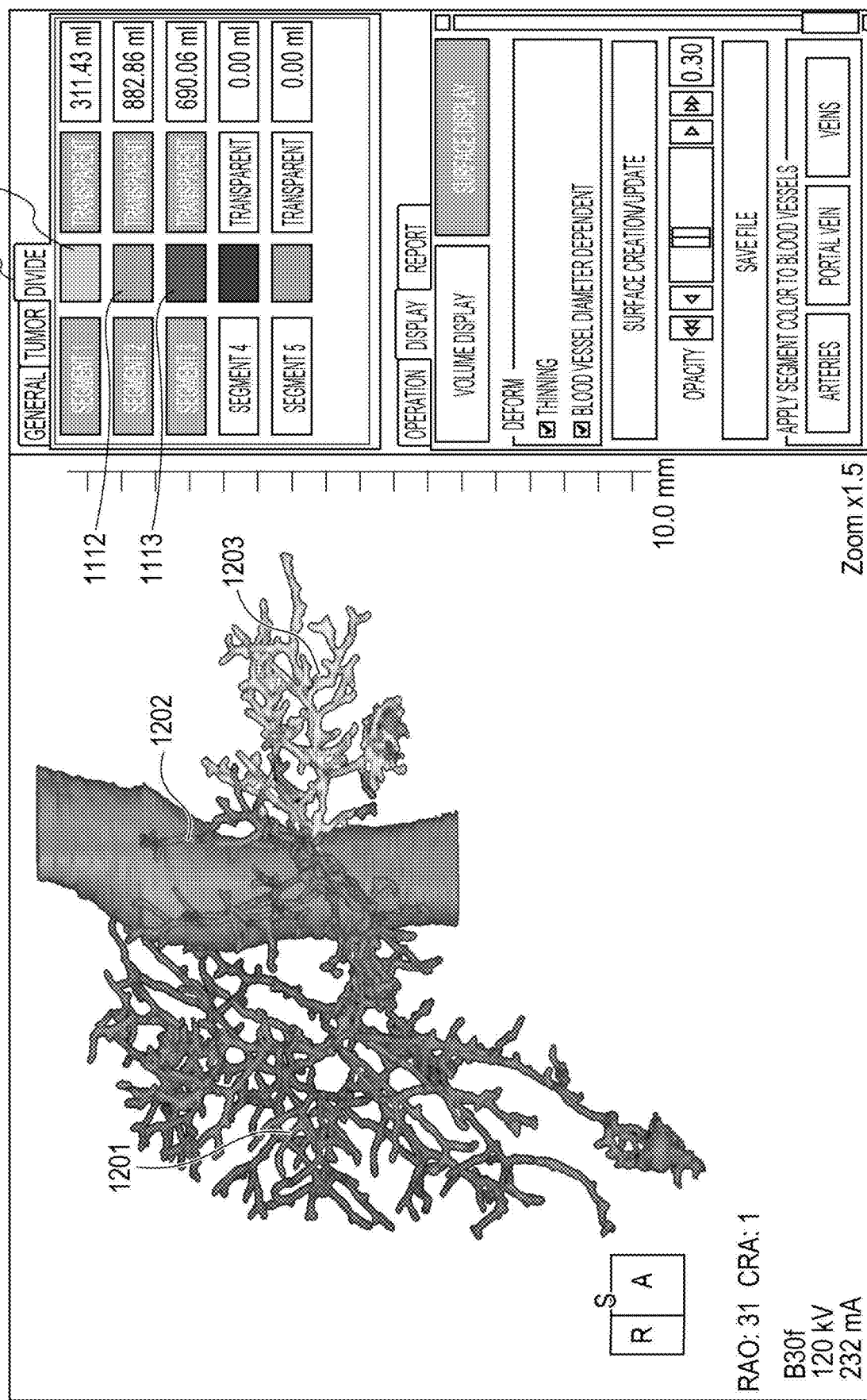
FIG. 12 shows an exemplary screen on which blood vessels are displayed in colors of corresponding segments where the blood vessels are located.

With this color information applied, if a surface creation button 1116 is pressed while a "thinning" checkbox 1114 and a "blood vessel diameter dependent" checkbox 1115 are selected, a transition to the screen shown in FIG. 12 takes place. In the exemplary screen shown in FIG. 12, blood vessels 1203 located in the "left hepatic vein perfusion segment 1103" are displayed in the color specified with the color information setting button 1111, blood vessels 1202 located in the "middle hepatic vein perfusion segment 1102" are displayed in the color specified with the color information setting button 1112, and blood vessels 1201 located in the "right hepatic vein perfusion segment 1101" are displayed in the color specified with the color information setting button 1113. The blood vessels shown in FIG. 12 are veins, but do not necessarily need to be veins. For example, a portal vein may be displayed instead. The segments are displayed in such a manner as to be identified by colors, but any other means can be used as long as it is possible to notify the user that they are different segments.

The surface shape data obtained by thinning the blood vessels is identifiably displayed in display mode depending on the segment of the liver. The course of blood vessels corresponding to one segment of the liver can thus be easily distinguished from that corresponding to another segment. In living liver transplantation, for example, this helps develop the surgical plan which takes into consideration the perfusion segment (i.e., segment of the liver) in the remnant liver of the donor (who gives the organ).

Although the "thinning" checkbox 1114 and the "blood vessel diameter dependent" checkbox 1115 are selected in this example, the blood vessels described above may be displayed in different colors with only the "thinning" checkbox 1114 selected.

The description of the first embodiment ends here.

Second Embodiment

In the first embodiment, flag information indicating whether to perform thinning is stored for each part (region) of an organ by the storage unit, and a part to be subjected to thinning is automatically identified and then the identified part is thinned. As thinning methods, the first embodiment has described a method by which a blood vessel is thinned by widening by a predetermined width in a direction orthogonal to the centerline of the blood vessel, and a method by which a blood vessel is thinned by widening the centerline in accordance with the blood vessel diameter. The second embodiment describes a method by which a blood vessel is displayed in thinned mode by gradually narrowing the diameter of the blood vessel with increasing distance from the origin toward the end of the blood vessel.

Figure 13:
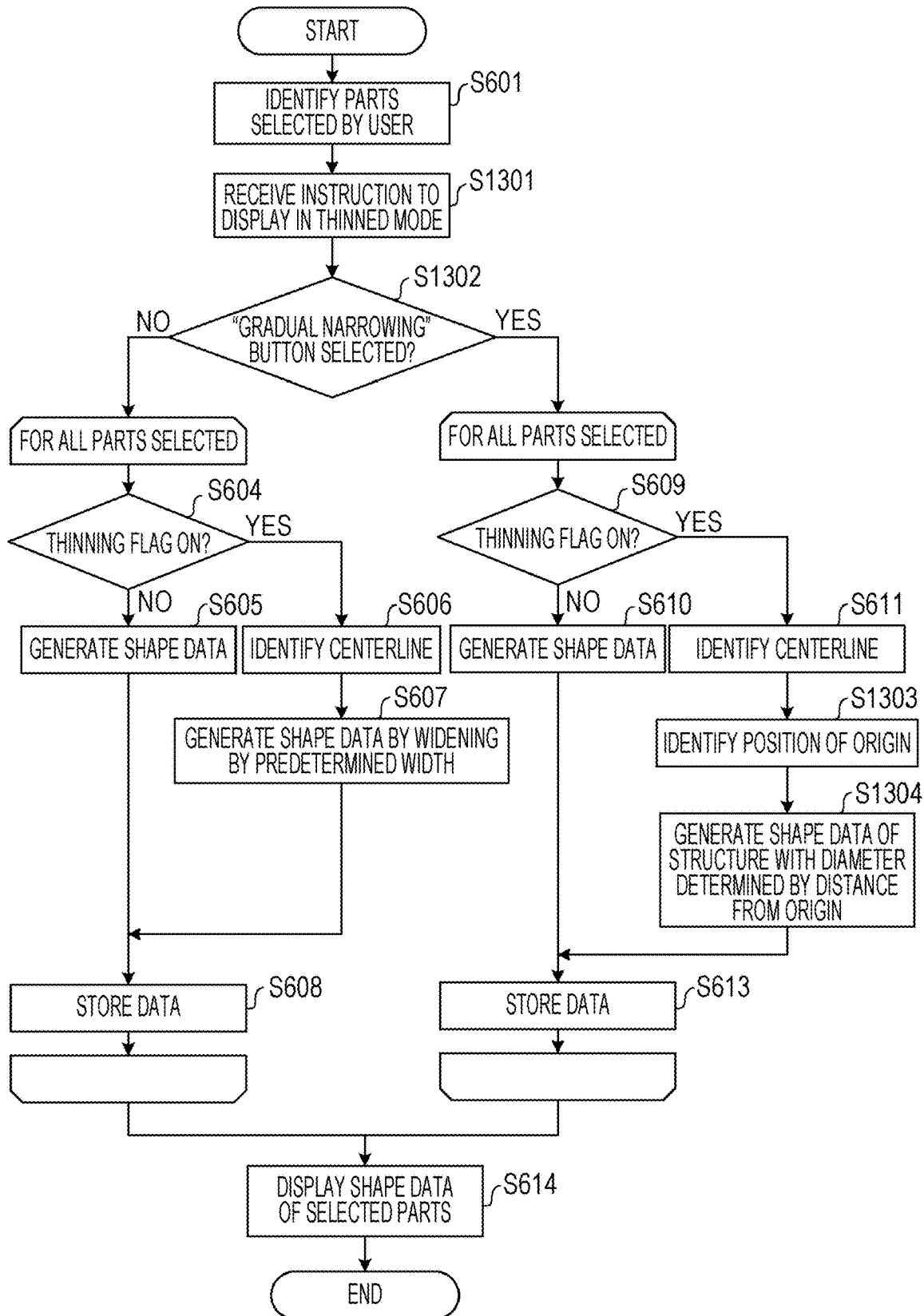
FIG. 13 is a flowchart illustrating a detailed flow of processing according to a second embodiment of the present invention.

The system configuration, hardware configuration, functional configuration, exemplary screens, and data table of the second embodiment are the same as those of the first embodiment, except that FIG. 6 is replaced by FIG. 13. The second embodiment describes only processing that differs from that of the first embodiment.

FIG. 13 is a flowchart illustrating a detailed flow of processing according to the second embodiment.

Step S601 and step S602 are not described here, as they are the same as those in the flowchart of FIG. 6.

Figure 14:
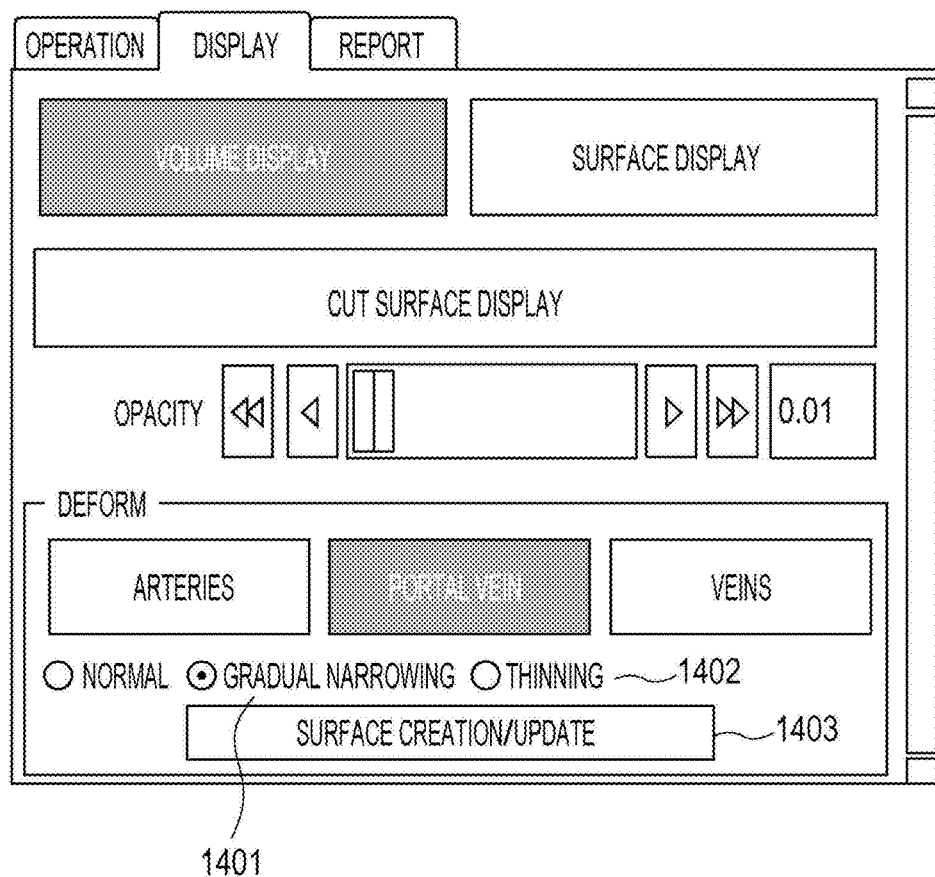
FIG. 14 is a schematic diagram of a portal vein, which is an exemplary part according to the second embodiment.

In step S1301, the CPU 201 of the medical image processing apparatus 100 determines whether an instruction to display an organ in thinned mode has been received. Specifically, the CPU 201 causes an instruction receiving screen 1400 (shown in FIG. 14) to be displayed on the display 210, and if a surface creation button 1403 is pressed while either a "gradual narrowing" button 1401 or a thinning button 1402 is selected, the CPU 201 determines that an instruction to display an organ in thinned mode has been received. If the surface creation button 1403 is pressed while a "normal" button is selected, the CPU 201 determines that a simple surface creation instruction, rather than the instruction to display an organ in thinned mode, has been received and then creates surface data on the basis of volume data.

When the surface creation button 1403 is pressed in step S1301, the CPU 201 of the medical image processing apparatus 100 determines, in step S1302, whether the "gradual narrowing" button 1401 is selected. If the CPU 201 determines that the "gradual narrowing" button 1401 is selected, the process proceeds to step S609, and otherwise proceeds to step S604.

Step S604 to step S611 are not described here, as they are the same as the corresponding steps in the first embodiment.

Figure 15:
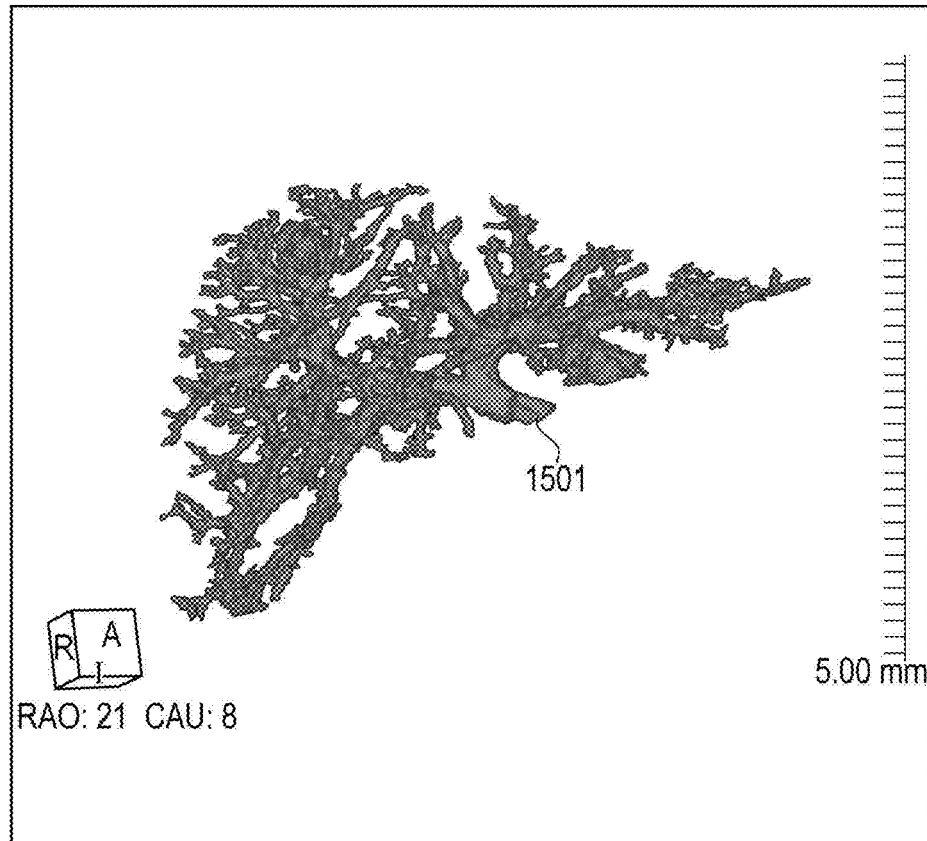
FIG. 15 is a schematic diagram illustrating an exemplary instruction receiving screen 1400 according to the second embodiment.

In step S1303, the CPU 201 of the medical image processing apparatus 100 identifies the position of an origin 1601 of the part for which the CPU 201 has determined in step S609 that the thinning flag is on (this corresponds to "origin identifying means"). The origin 1601 is the starting point (or root) of the tree structure of the part, which is a tubular structure. For example, the portion indicated by reference numeral 1501 in FIG. 15 is the origin of the portal vein of the liver. The position of the origin 1601 may be identified by a technique which receives an input from the user via a pointing device, such as a mouse, or by a known technique (see, e.g., Japanese Patent Laid-Open No. 2012-228396) which automatically extracts the position of the origin 1601 of the tubular structure, such as the portal vein having a tree structure.

In step S1304, from the part (tree structure) for which the CPU 201 has determined in step S609 that the thinning flag is on, the CPU 201 generates shape data representing a diameter determined in accordance with distance from the origin 1601.

The processing performed here is described in detail. On the basis of the position of the origin 1601 of the part identified in step S1303, the CPU 201 of the medical image processing apparatus 100 extracts the tree structure of the part. The tree structure is extracted in the following manner. The CPU 201 extracts voxels corresponding to the centerline identified in step S611. Of the extracted voxels, one that corresponds to the position of the origin 1601 identified in step S1303 is defined as the starting point, and a series of other voxels running therefrom is scanned. This operation is described using the schematic diagram of FIG. 16. The CPU 201 identifies voxels running from the origin 1601. If the number of voxels running from the origin 1601 is one or two, the CPU 201 identifies the one or two voxels as a voxel (or voxels) of the same linear structure element. This operation is repeated and if the CPU 201 identifies a voxel 1602 that is the third or subsequent one from the origin 1601, the CPU 201 identifies the voxel 1602 as a node. The CPU 201 can identify the node 1602 and a node 1603 (see FIG. 16) by repeating this operation. By the CPU 201, voxels running form the origin 1601 to the node 1602 are extracted as a linear structure element 1611, voxels running form the node 1602 to a node 1603 are extracted as a linear structure element 1612, voxels running form the node 1602 to an end point 1604 are extracted as a linear structure element 1613, voxels running form the node 1603 to an end point 1606 are extracted as a linear structure element 1614, and voxels running form the node 1603 to an end point 1605 are extracted as a linear structure element 1615.

The tree structure may be extracted by other techniques, such as those using a Hessian matrix. Specifically, after performing multi-resolution transformation on a three-dimensional medical image, the CPU 201 performs eigenvalue analysis of the Hessian matrix in images of respective resolutions to extract linear structure elements. Next, by combining together the results of analysis in the images of respective resolutions, the CPU 201 extracts linear structure elements of various sizes in the three-dimensional medical image. Then, by connecting the extracted linear structure elements using, for example, a minimum spanning tree algorithm, the CPU 201 can obtain data representing the tubular structure in the three-dimensional medical image (see, e.g., Japanese Patent Laid-Open No. 2012-223338).

Figure 16:
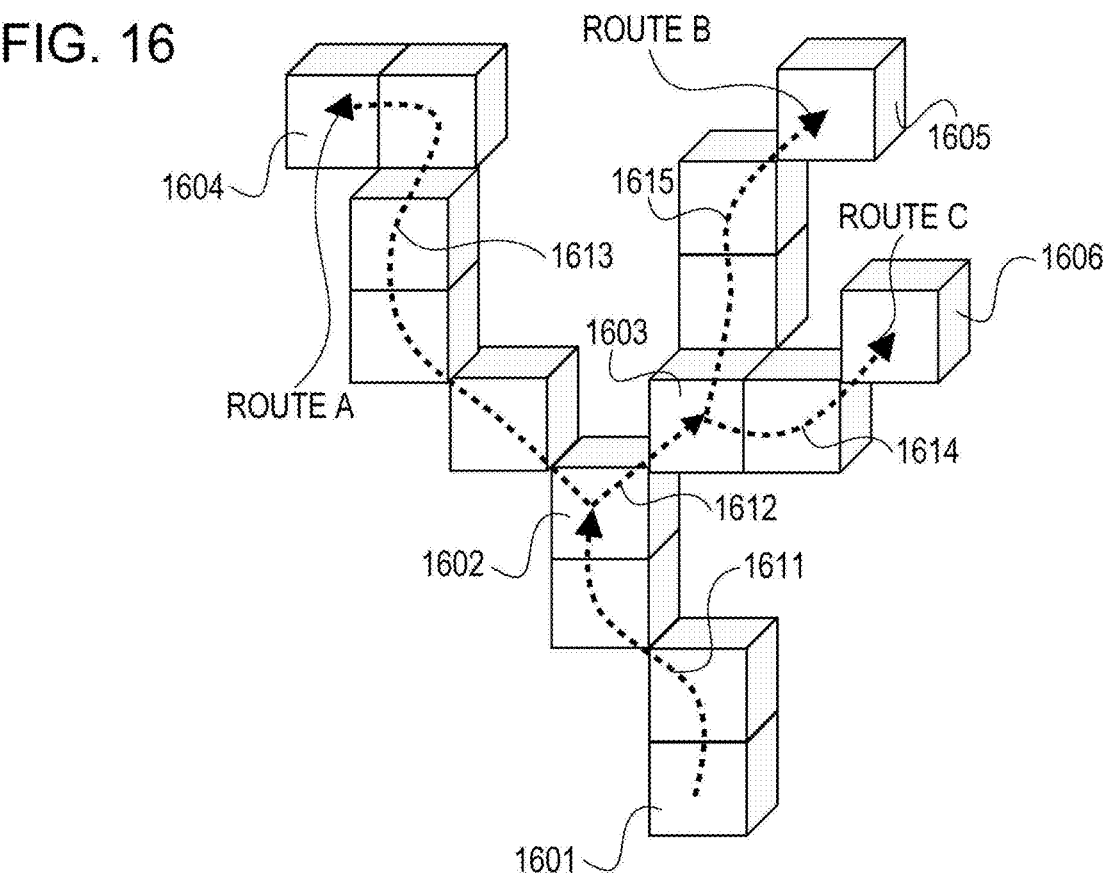
FIG. 16 is a schematic diagram used in the explanation of routes according to the second embodiment.

Next, the CPU 201 identifies a plurality of routes (paths) that extend from the origin 1601 of the extracted tree structure of the part to reach the end point. Route A illustrated in FIG. 16 is a route that originates at the origin 1601 and passes through the node 1602 to reach the end point 1604. Route B is a route that originates at the origin 1601 and passes through the node 1602 and the node 1603 to reach the end point 1605. Route C is a route that originates at the origin 1601 and passes through the node 1602 and the node 1603 to reach the end point 1606. In the schematic diagram of FIG. 16, the CPU 201 can identify the three routes described above.

The CPU 201 determines the length of each of the plurality of routes identified as described above. From the lengths determined, the CPU 201 identifies the longest route in length from the origin to the end point. The present embodiment is described on the assumption that route A is the longest one. The CPU 201 determines, by calculation over the range from the origin to the end point of route A, the radius of the part in a cross-section thereof orthogonal to the centerline identified in step S611. Of all the radii determined, the largest one (hereinafter referred to as "largest radius") and the smallest one (hereinafter referred to as "smallest radius") are identified by the CPU 201.

On the basis of the largest and smallest radii identified, the CPU 201 identifies the radius decrease rate per voxel with respect to the distance of route A. For example, the CPU 201 can identify the radius decrease rate per voxel by dividing the value obtained by subtracting the smallest radius from the largest radius, by the distance of route A. The radius decrease rate per voxel can be determined from the largest radius, the smallest radius, and the distance of route A as described above. However, this is merely an example and is not necessarily the only way to determine. Although the radius has been used in the description of the present embodiment, the method described above may of course be implemented using the diameter.

Then first, for the shortest of all the plurality of routes identified, the CPU 201 determines the radius of the centerline. The present embodiment is described on the assumption that route C is the shortest one.

The CPU 201 determines the radius of the part at the position of the origin 1601 identified in step S1303 (hereinafter this radius is referred to as "origin radius"). From this origin radius and the decrease rate per voxel, the CPU 201 determines the radius of the centerline running along route C, by calculation for each of the voxels running from the origin 1601 to the end point 1606. The CPU 201 thus determines the radius of each of the linear structure element 1611, the linear structure element 1612, and the linear structure element 1614. The radii determined here are never changed.

Next, the CPU 201 identifies the next shortest route after route C. This is route B in the present embodiment. Of the radii of all the linear structure elements forming route B, the radii of the linear structure element 1611 and linear structure element 1612 are already determined by the calculation for route C. Therefore, the CPU 201 determines the radius of only the linear structure element 1615 by calculation. On the basis of the radius at the node 1603 determined by the calculation for route C and the decrease rate per voxel, the CPU 201 determines the radius of the linear structure element 1615.

Next, the CPU 201 identifies the next shortest route after route B. This is route A in the present embodiment. Of the radii of the linear structure elements forming route A, the radius of the linear structure element 1611 is already determined. Therefore, the CPU 201 determines the radius of the linear structure element 1613 by calculation on the basis of the decrease rate per voxel and the radius at the node 1602 described above. The CPU 201 then determines whether there is the next longest route after route A. Since there is no route longer than route A in FIG. 16 of the present embodiment, the CPU 201 ends the processing here.

Figure 17:
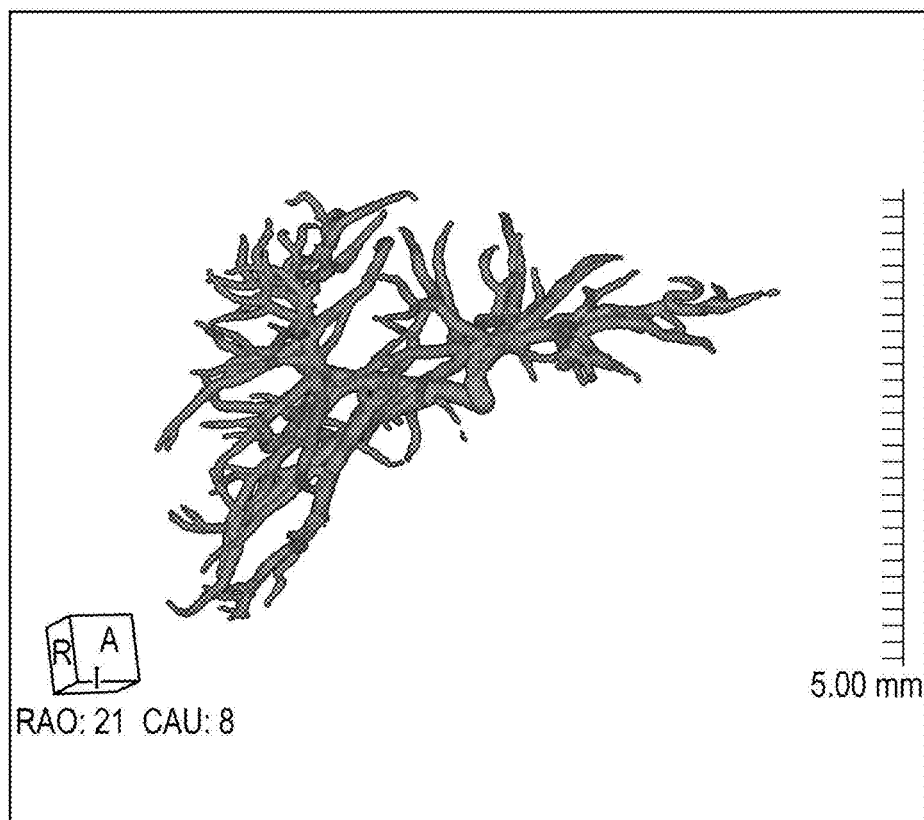
FIG. 17 is a schematic diagram of a portal vein obtained by thinning using a diameter that varies with distance from the origin.

This completes the thinning process which involves gradually narrowing the radius of the part in accordance with distance from the origin of the part. The schematic diagram of FIG. 17 shows a portal vein obtained by thinning which involves gradually narrowing the radius of the part in accordance with distance from the origin of the part. The thinning which involves gradually narrowing the diameter in accordance with distance from the origin is advantageous in that even when parts are ones that branch out intricately, they are displayed in such a manner that the diameters of the regions (i.e., the outer perimeters of the tubular structures) that are equidistant from the origin are equal. This means that if the outer perimeters are equal, the user can instinctively determine that the distances from the origin are equal. In other words, the user can instinctively perceive the positional relation with respect to the origin.

The description of the second embodiment ends here.

The present invention makes it possible to provide a mechanism that can facilitate thinning and display of a region the user wants to display in thinned mode.

Although the liver has been described as an organ in the present embodiment, any other organs (e.g., heart, brain, and lungs) can be included in the present invention as long as they are tubular structures.

The present invention may be embodied, for example, as a system, an apparatus, a method, a program, or a storage medium. Specifically, the present invention may be applied to a system composed of a plurality of devices, or to an apparatus composed of a single device. The present invention includes the case of directly or remotely supplying a software program that implements the functions of the above-described embodiments to a system or apparatus. The present invention also includes the case of being achieved when an information processor of the system or apparatus reads out and executes the supplied program code.

Therefore, the program code installed in the information processor for implementing functional processing of the present invention in the information processor also implements the present invention. That is, the present invention also includes a computer program for implementing the functional processing of the present invention.

In this case, the computer program may be object code, a program executed by an interpreter, or script data supplied to an OS, or may be of any other form as long as it functions as a program.

Examples of a recording medium for supplying the program include a flexible disk, a hard disk, an optical disc, a magneto-optical disc, an MO, a CD-ROM, a CD-R, and a CD-RW. The examples also include a magnetic tape, a nonvolatile memory card, a ROM, and a DVD (DVD-ROM, DVD-R).

The program may be supplied by connecting to a website on the Internet using a browser on a client computer, and then downloading the computer program of the present invention or a compressed file having an automatic installation function, from the website onto a recording medium, such as a hard disk.

The present invention may also be implemented by dividing the program code forming the program of the present invention into multiple files, and downloading the multiple files from different websites. That is, the present invention also includes a WWW server that allows multiple users to download program files for implementing the functional processing of the present invention in the information processor.

The program according to the present invention may be encrypted and stored on a storage medium, such as a CD-ROM, and distributed to users. In this case, users satisfying predetermined conditions are permitted to download key information for decrypting the encrypted program from a website via the Internet. By using the downloaded key information, the encrypted program can be executed, installed onto the information processor, and implemented.

The functions of the embodiments described above are implemented when the information processor executes a read-out program. The functions of the embodiments described above may also be implemented when an OS or the like running on the information processor performs part or all of actual processing on the basis of instructions of the program.

The functions of the embodiments described above may also be implemented when the program read out from a recording medium is written to a memory of a function expansion board inserted in the information processor or a function expansion unit connected to the information processor, and then a CPU or the like of the function expansion board or the function expansion unit performs part or all of actual processing on the basis of instructions of the program.

The present invention makes it possible to provide a mechanism that can facilitate thinning and display of a region the user wants to display in thinned mode.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A medical image processing apparatus comprising:
   at least one processor; and
   a memory that stores a program which, when executed by the at least one processor, causes the at least one processor to:
   acquire medical image data;
   receive an instruction for selecting an analysis function from a user;
   determine which of a plurality of tubular structures is to be subjected to thinning in the medical image data based on the selected analysis function and information corresponding to a type of the analysis function, wherein the information, corresponding to the type of the analysis function, is information about which of a plurality of tubular structures in an organ is to be subjected to thinning; and
   display the organ in such a manner that an image of a tubular structure to be subjected to thinning is displayed differently from an image of a tubular structure not subjected to thinning.

2. The medical image processing apparatus according to claim 1, wherein the at least one processor further performs control in such a manner that the tubular structure to which the thinning process has been applied is displayed in a color indicated based on color information.

3. The medical image processing apparatus according to claim 1, wherein the at least one processor performs control to cause the display not to display a tubular structure which is not selected by the user.

4. The medical image processing apparatus according to claim 1, wherein at least a part of the tubular structure to which the thinning processing has been applied has a diameter which is smaller than a diameter of an actual tubular structure.

5. The medical image processing apparatus according to claim 1, wherein the at least one processor performs control to display an image including the organ which is overlapped with the tubular structure to which the thinning processing has been applied on the display.

6. The medical image processing apparatus according to claim 1, wherein the at least one processor performs control in such a manner that either one of the image of the tubular structure to be subjected to thinning and the image of the tubular structure not subjected to thinning determined by the determining means is displayed.

7. The medical image processing apparatus according to claim 1, wherein the at least one processor performs control in such a manner that either one of display the image of the tubular structure to be subjected to thinning and the image of the tubular structure not subjected to thinning determined by the determining means is not displayed.

8. A medical image processing method comprising:
   acquiring medical image data;
   receiving an instruction for selecting an analysis function from a user;
   determining which of a plurality of tubular structures is to be subjected to thinning in the medical image data based on the selected analysis function and information corresponding to a type of the analysis function, wherein the information, corresponding to the type of the analysis function, is information about which of a plurality of tubular structures in an organ is to be subjected to thinning; and
   displaying the organ in such a manner that an image of a tubular structure to be subjected to thinning is displayed differently from an image of a tubular structure not subjected to thinning.

9. A non-transitory computer readable storage medium for causing a computer to execute a medical image processing method, the method comprising:
- acquiring medical image data;
- receiving an instruction for selecting an analysis function from a user;
- determining which of the a plurality of tubular structures is to be subjected to thinning in the medical image data based on the selected analysis function and information corresponding to a type of the analysis function, wherein the information, corresponding to the type of the analysis function, is information about which of a plurality of tubular structures in an organ is to be subjected to thinning; and
- displaying the organ in such a manner that an image of a tubular structure to be subjected to thinning is displayed differently from an image of a tubular structure not subjected to thinning.

* * * * *